United States Patent [19]
Thompson et al.

[11] Patent Number: 5,825,479
[45] Date of Patent: Oct. 20, 1998

[54] APPARATUS FOR DETECTING FIBERS WITH DIFFERENT DISPERSION CHARACTERISTICS AND METHOD

[75] Inventors: Leo J. Thompson, Lilburn; Emmanuel Anemogiannis, Atlanta, both of Ga.

[73] Assignee: VeriFiber Technologies, Inc., Duluth, Ga.

[21] Appl. No.: 876,505

[22] Filed: Jun. 16, 1997

[51] Int. Cl.$^6$ .................................................. G01N 21/84
[52] U.S. Cl. ............................................................ 356/73.1
[58] Field of Search ............................................. 356/73.1

[56] References Cited

U.S. PATENT DOCUMENTS 4,710,022  12/1987  Soeda et al. .......................... 356/73.1

Primary Examiner—Vincent P. McGraw
Attorney, Agent, or Firm—Steven C. Stewart; William A. Marvin

[57] ABSTRACT

A method and apparatus for distinguishing between fiber types having different dispersion characteristics and arbitrary lengths is disclosed. An optical pulse having a predetermined wavelength and predetermined time width is propagated through the fiber and then detected. The optical pulse after being fed through the fiber is measured at different wavelengths along with the length of the fiber. If the measured pulse is within a predetermined amount at the determined length, then fiber under test corresponds to a type having a first dispersion characteristic. If it is determined that the measured pulse is within a second amount, then the fiber under test corresponds to a type having a second dispersion characteristic. Alternately one or more optical pulses of arbitrary width each having different wavelengths after being propagated through the fiber under test is fed through a plurality of filters and detected. The wavelength of the pulse of the smallest time duration is detected and a corresponding dispersion characteristic is then indicated.

15 Claims, 3 Drawing Sheets

APPARATUS FOR DETECTING FIBERS WITH DIFFERENT DISPERSION CHARACTERISTICS AND METHOD

BACKGROUND OF THE INVENTION

This application relates to an apparatus and method for detecting different optical fibers types and more specifically to a distinguishing between optical fibers having different dispersion characteristics.

Optical fiber have a characteristic called dispersion. This dispersion characteristic causes laser light phase when transmitted through a fiber at a predetermined frequency and an initial phase to vary as a function of the length of the fiber. It is desirable when transmitting a laser light signal through the fiber that the phase of the signal at the fiber output be the same as the phase at the fiber input. In order to compensate for this variance, a short stand fiber, which contains material that compensates for the dispersion characteristic is connected to the output of the fiber. The material of this short fiber strand is typically very expensive and has high inherent. New types of fiber are being developed to reduce the inherent loss of the fiber while compensating for dispersion as a function of frequency.

When designing networks it is desirable to incorporate these new fiber types that compensate for dispersion in the networks. Many new optical fibers are being developed to compensate for the dispersion as a function of the frequency of the optical carrier being fed through the fiber. These new fibers may be marked on their cover to indicate the frequency at which it varies the dispersion. But when the fibers are wrapped in a bundle, it is difficult to read the markings and to detect the wavelength that the fiber will vary the dispersion characteristic of the optical signal.

SUMMARY OF THE INVENTION

An object of this invention is to provide an improved method and apparatus for detecting different optical fiber types;

Another object of this invention is to distinguish the dispersion characteristics of multiple fibers;

A further object of this invention is to provide a method and apparatus for identifying and distinguishing one fiber with specific dispersion characteristics within a set of fibers each having arbitrary dispersion characteristics;

It is an additional object of this invention to identify a fiber by its dispersion characteristics and then compute the fibers dispersion length product; and It is also an object of this invention to determining which fiber in a plurality of fibers wrapped in a bundle has a desired dispersion characteristics.

These and other objects are provided with a method for distinguishing between given set of fiber types having different dispersion characteristics. In this method a pulse of laser light having a predetermined frequency and a predetermined pulse width is transmitted through a fiber under test. The pulse is then detected after passing through the fiber and the width of the pulse is measured. If the measured width is less than a predetermined amount then the test fiber corresponds to a type with a first dispersion characteristic. If the measured width is greater than the predetermined amount then the test fiber corresponds to a type with a second dispersion characteristic.

Another embodiment of the invention has an apparatus for distinguishing between fiber types having different dispersion characteristics. The apparatus has a device for transmitting through a test fiber a pulse of laser light having a predetermined wavelength. A detector detects the pulse width of the laser light after passing through the fiber, and measures the detected pulse width at predetermined wavelength. An electric signal comparator then determines whether the test fiber corresponds to a type with a first dispersion characteristic if the width of the first frequency pulse is less than every other measured pulse width, and determines whether the fiber corresponds to a type with a second dispersion characteristic if the width of the second frequency pulse is less than every other measured pulse width.

DESCRIPTION OF THE PREFERRED EMBODIMENTS

Figure 1:
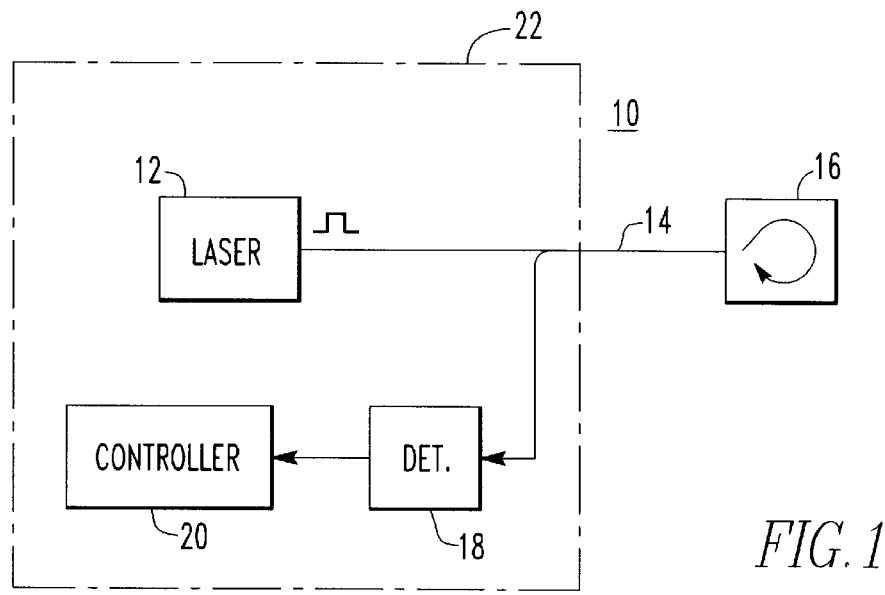
FIG. 1 is a schematic diagram of a system for testing the dispersion characteristics of a fiber in accordance with the invention.

Referring to FIG. 1 there is shown a system 10 for distinguishing between a fiber 14 under test having one of many different dispersion characteristics. The system 10 has a conventional Laser 12 or other light source that generates an input pulse of an optical signal at a predetermined width and at a predetermined optical wavelength. The input pulse is then inserted into test fiber 14. An example laser is model number FU-627SLD-F manufactured by Mitsubishi, Inc. of Japan. The pulse having a typical width of 0.5–1.0 ns and wavelength of 1550 nm is fed through test fiber 14 to determine the test fiber's 14 dispersion characteristic. The optical signal after propagating through the fiber exits the other end of test fiber 14 and is detected at that location, or preferably is reflected back into the test fiber 14 with a conventional reflector 16. The optical signal exiting test fiber 14 is referred to herein as the output pulse.

The output pulse is fed through a diode detector 18, which converts the output pulse into an electrical signal. Optionally the input pulse is also fed to diode detector 18. The electrical signal from detector 18 is then fed to device 20. Device 20 measures the total propagation time of the output pulse to determine the length of the fiber. Device 20 preferable has a clocked gate or other sampling device that detects the width of the reflected output pulse. Preferably Laser 12, detector 18 and device 20 are located within a common enclosure 22.

Due to the inherent nature of test fiber 14, it has been determined that for the measured fiber length if the measured predetermined output pulse width is less than a predetermined amount, then the test fiber would correspond to a first fiber type. if it is determined that the measured predetermined output pulse width is greater than a first predetermined amount, then the test fiber would correspond to a second fiber type.

If more than two test fibers were being tested, the measured reflected detected pulse width would fall within a predetermined range as a function of the type of test fiber detected. The range as a function of the measured fiber length and pulse width could be programmed into a table and looked up, or displayed using a computer preferably located in device 20. For example, if three fiber types were being tested and if the output pulse width was within a first predetermined time range, than device 20 would provide an indication that the test fiber corresponds to a first type. If the output pulse width was within a second predetermined time range, then device 20 would indicate that the test fiber corresponds to a second type. If the output pulse width was within a third predetermined time range, then device 20 would indicate that the test fiber corresponds to a third type. These indications could be provided by an indicator (not shown) coupled to device 20. Example indicators include a personal computer, a handheld display, LED indication or other conventional methods.

Figure 2:
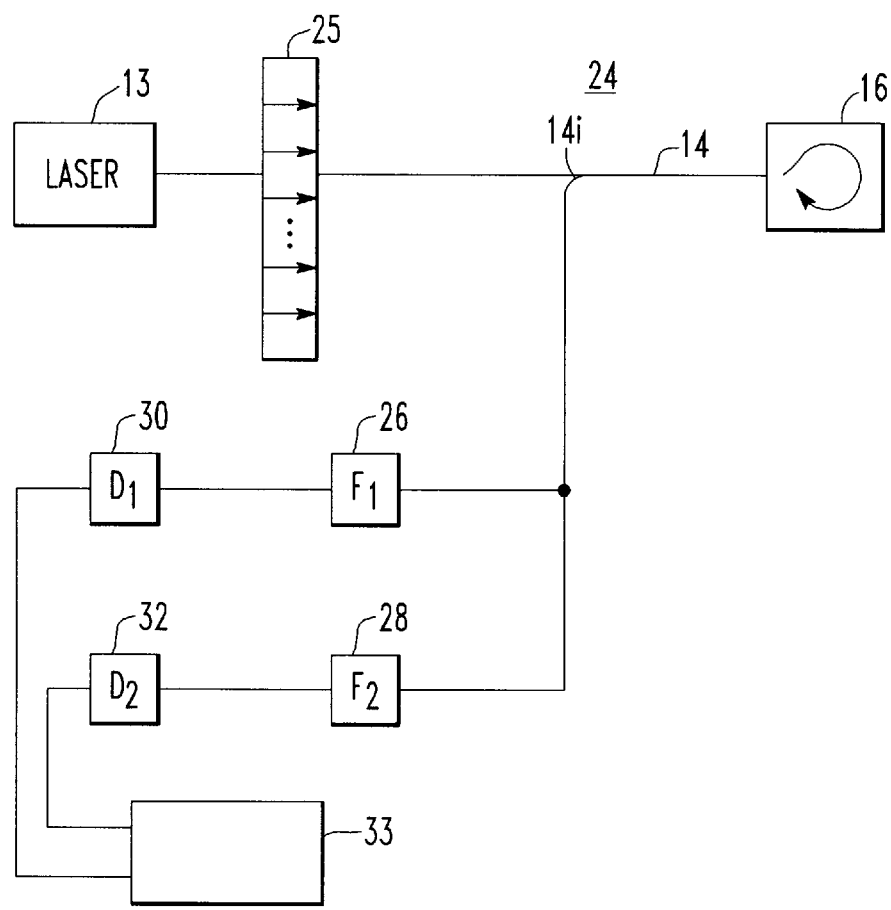
FIG. 2 is a schematic diagram of an alternate embodiment of a system for detecting the dispersion characteristics of a fiber in accordance with the invention.

Referring to FIG. 2, there is shown another device 24 for detecting the type of fiber 14 under test. Device 24 has a light source 13, which generates a pulsed input optical signal at many predetermined wavelengths and a pulse with either an arbitrary or a predetermined width. This input optical signal is fed through fiber 14. Preferably device 24 has light source 13 containing a tunable spectrum laser that generates a pulsed input signal that can be tuned to various wavelengths using conventional means. In another embodiment of the invention light source 13 may be composed of multiple lasers that each have their own unique output frequency. In another embodiment of the invention, light source 13 may be an LED generating a pulsed input optical signal having a broad spectrum output.

The optical signal from light source 13, before being fed through test fiber 14, when generated using a broad light source may be passed through optional input filter 25, also referred to as a filter bank, comprised of multiple wavelength bandpass filters to generate input optical signals having multiple narrow wavelengths. The central wavelengths of these filters correspond to the wavelengths where the various fibers under test have zero dispersion. The pulsed input optical signal are fed through input filter 25, through fiber 14 and reflected using reflector 16.

Optical bandpass wave-length filters 26 and 28 are preferably connected near the input side (14i) of test fiber 14. Alternately filters 26 and 28 are arranged in an array and may be inserted in place of and at the location of reflector 16 to receive the optical signal exiting at the far end of test fiber 14. Filters 26 and 28 are tuned on the zero-dispersion wavelength of the different fiber types being tested to permit the optical signal in fiber 14 to pass to detector 30 and 32, respectively. For the case of the broad bandwidth light source 13 i.e. an LED, an optional band-pass wavelength filter array 25 is used and filters 26 and 28 have identical characteristics to the filters in bank 25.

Detectors 30 and 32 detect the width of optical pulse input signal and feed a signal indicating the width to comparator 33. Comparator 33 then provides an indication, using conventional means, (i.e. LED display, feeding a signal to a computer, etc.) which of the detectors 30 or 32 has detected the smaller pulse width. Although two detectors 30 and 32 and two filters 26 and 28 are shown, this invention contemplates having multiple filters connected to respective detectors.

If comparator 33 determines that detector 30 sensed the pulse of the reflected optical signal with a width less than the pulse of the reflected optical signal sensed by detector 32, then comparator 33 would indicate that the fiber 14 is of a first type. If comparator 33 determines that detector 32 sensed that the pulse of the reflected optical signal has a width less than the pulse of the input optical signal sensed by detector 30, then comparator would indicate that fiber 14 is of a second type. If more than two input filters 25 were used along with more than two output filters, comparator 33 determine which of the detectors had the shortest pulse and would then provide indication of the fiber under test accordingly.

Comparator 33 can product a dispersion-length product of the fiber under test. In which case comparator 33 would contain a timer that would measure the time between the launch of the input pulse and the arrival of the reflected pulse. The comparator would contain a processor to multiply the measured time by the speed of light constant divided by one and a half to determine the test fiber length. The test fiber length would then be multiplied by a dispersion value corresponding to the type of the detected test fiber and displayed using conventional means.

Figure 3:
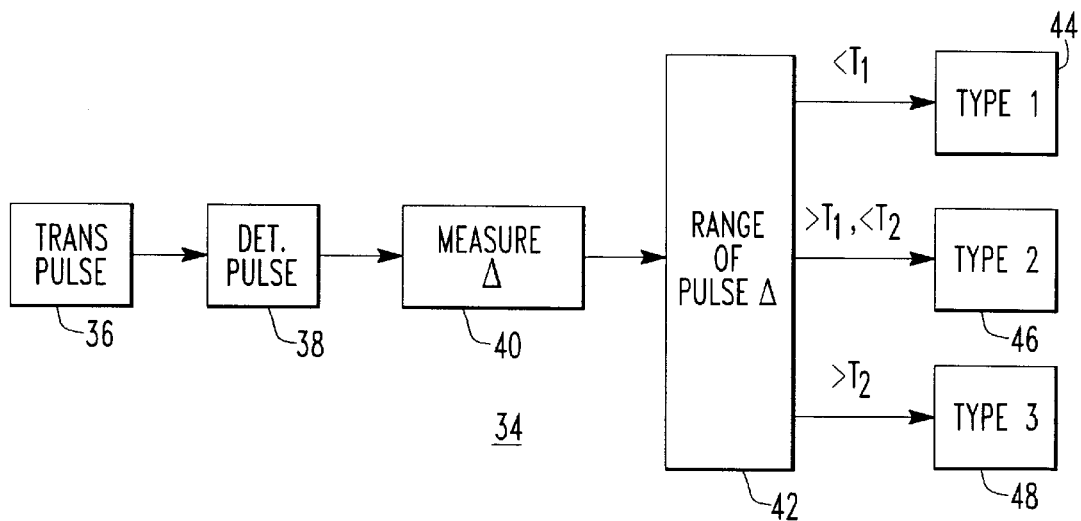
FIG. 3 is a flow diagram showing the steps in distinguishing between fiber types having different dispersion characteristics.

Referring to FIG. 3, there is shown a flow diagram 34 of the method for distinguishing between test fiber 14 having different dispersion characteristics using the system 10 shown in FIG. 1. In this method's first step 36, an optical input pulse having a predetermined wavelength and a predetermined pulse width is transmitted through a test fiber 14 (See FIG. 1). Next the pulse width in step 38 of the detected optical output pulse is detected after propagating through the test fiber 14.

In step 40, the time width of the detected output pulse is determined by device 20. Also the length of test fiber 14 is determined by multiplying the time difference between the occurrence of the rising edges of the input pulse and output pulse by the speed of light constant divided by 1.5.

In step 42, device 20 checks a table to determine if the measured output pulse width at the determined length is less than a first predetermined amount. The values for the table are preset in a memory (i.e. ROM, EPROM, etc.) using convention means by computing the time values of a predetermined pulse propagating through fiber types of various dispersion characteristics and having different fiber lengths. The values are computed using techniques such as those described in chapter twelve of *Light Transmission Optics*, second edition, by D. Marcuse, Robert E. Krieger Publishing Company Inc. (1989). If the width is less than a first predetermined amount, device 20 indicates that the test fiber 14 corresponds to a type with a first dispersion characteristic in step 44. If device 20 determines by referring to the table, that the measured pulse width at the determined length is greater than a second predetermined amount then device 20 indicates that the test fiber corresponds to a type with a third dispersion characteristic in step 48. If after referring to the table, the measured pulse width is between the first predetermined amount and the second predetermined amount at the determined length, then device 20 indicates that the test fiber 14 corresponds to a fiber type with a second dispersion characteristic in step 46. Alternately after determining the type of the test fiber 14, device 20 could multiply the determined length by the test fiber's dispersion value and display the value using conventional means.

Figure 4:
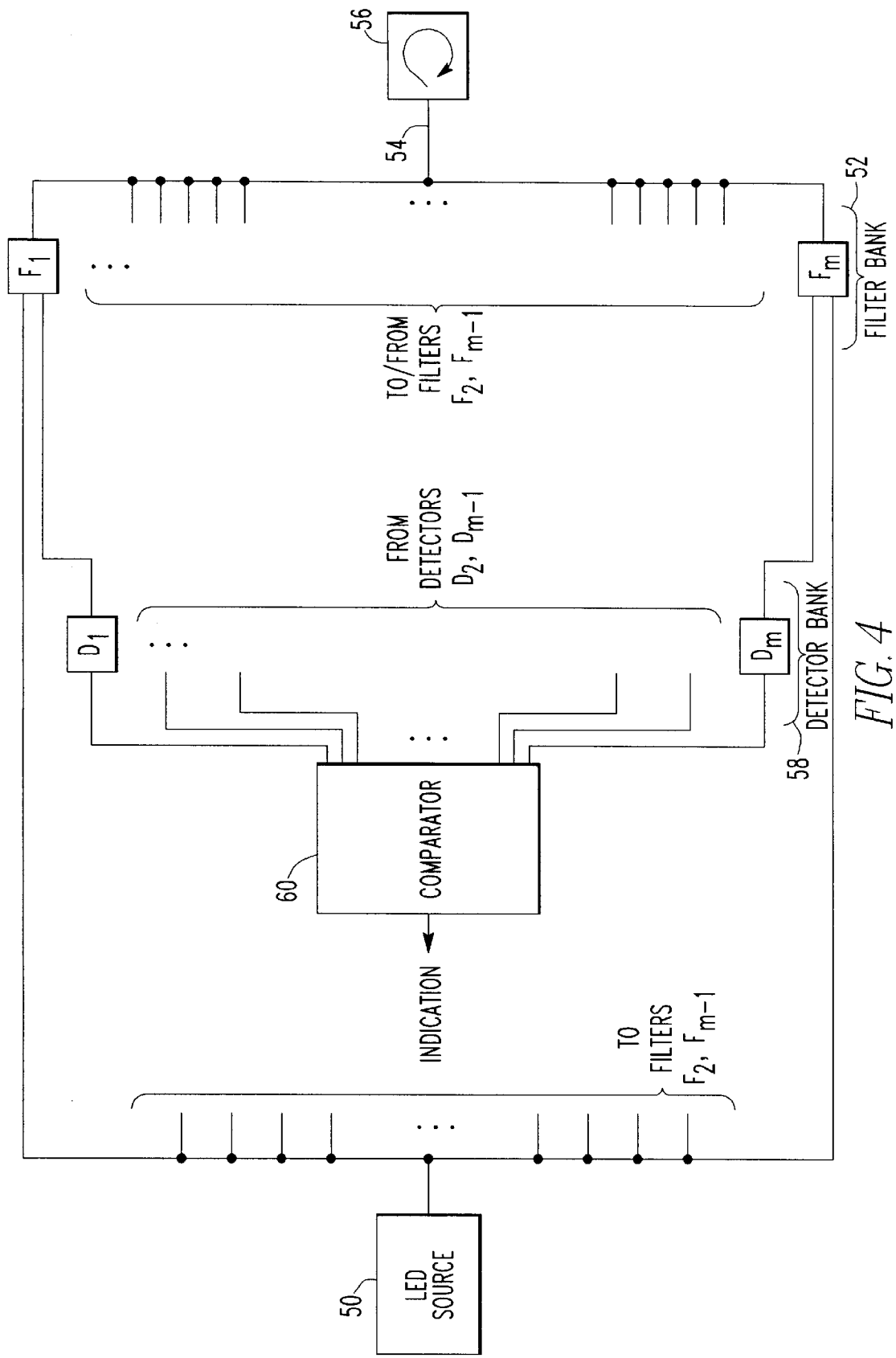
FIG. 4 is a simplified schematic diagram of an alternate embodiment of the invention shown in FIG. 2.

Referring to FIG. 4, there is shown another alternate embodiment of the invention 49 having a wide spectral LED light source 50. The source 50 generates an optical signal pulse that is fed through band-pass wavelength filter bank 52 and into test fiber 54. The optical signal pulse propagates through test fiber 54 and reflected back using reflector device 56. The optical signal pulses are then fed back through filters 52 and detected by a respective array of detectors 58, where one detector is associated with each filter. The detectors convert the optical signal pulses into an electrical signal and fed the converted signal to comparator 60. Comparator 60 determines which detector senses the shortest optical signal pulse. The specific detector that is associate with the filter whose bandwidth includes the wavelength for which fiber 54 has zero dispersion. Comparator then provides an indication using conventional methods of the corresponding test fiber 54.

While the principles of the invention have been made clear in the illustrated embodiments, there will be immediately obvious to those skilled in the art, many modifications are stcuctured arrangements proportions, elements, materials, and components used in the practice of the invention, in otherwise which are particularly adapted for specific environments and operational requirements, without departing from those principals. The appended claims are therefore intended to cover and embrace any such modifications within the limits only of the true spirit and scope of the invention.

What is claimed is:

1. A method for distinguishing between fiber types having different dispersion characteristics, the method comprising the steps of:

transmitting through a fiber under test an optical pulse having a predetermined wavelength and a predetermined pulse width;

detecting the pulse width of the optical pulse after passing through the fiber;

measuring the time duration of the detected optical pulse width; and indicating a dispersion characteristic type of the fiber under test if the measured time duration is within a predetermined range.

2. The method as recited in claim 1 further comprising the step of indicating that the fiber under test has a second dispersion characteristic if the measured time duration is greater than the predetermined amount.

3. The method as recited in claim 1 further comprising the steps of:

transmitting a second optical pulse having the predetermined wavelength and having a second predetermined pulse width into the fiber under test;

detecting the second pulse width of the optical pulse after propagating through the fiber;

measuring the time duration of the second detected pulse width;

indicating that the fiber under test has a first dispersion characteristic if the measured duration of the second detected pulse width is less than or equal to a second predetermined amount; and indicating that the fiber under test has a second dispersion characteristic if the measured duration of the second detected pulse width is greater than the second predetermined amount.

4. The method as recited in claim 1 further comprising the step of determining that the test fiber corresponds to a type with a second dispersion characteristic if the measured duration of the second detected pulse width is within a third predetermined range.

5. The method as recited in claim 1 further comprising the steps of:

detecting the optical pulse upon entering the fiber under test and detecting the pulse after propagating through the fiber under test;

determining the time difference between when the pulse entering the fiber and the pulse propagating through the fiber under test;

computing the length of the fiber under test by multiplying the determined time difference by a constant; and indicating a dispersion characteristic type of the fiber under test if the measured pulse time duration is within a predetermined range for a computed fiber length.

6. The method as recited in claim 5 further comprising the step of computing a dispersion-length product by multiplying the fiber length by a value corresponding to the determined dispersion characteristic of the fiber under test.

7. An apparatus for distinguishing between fiber types having different dispersion characteristics comprising:

means for transmitting through a test fiber an optical pulse having a predetermined wavelength and a predetermined pulse width;

means for detecting the pulse width of the optical pulse after passing through the fiber;

means for measuring the detected pulse width;

means for determining the length of the fiber; and means for indicating that the test fiber corresponds to a type with a first dispersion characteristic if the measured detected pulse width is within a predetermined amount for the determined fiber length.

8. The apparatus as recited in claim 7 further comprising means for indicating that the test fiber corresponds to a type with another dispersion characteristic if the measured difference is within a second predetermined amount for the determined fiber length.

9. The apparatus as recited in claim 7 wherein the transmitting means includes a diode laser.

10. The apparatus as recited in claim 7 wherein the detecting means includes a photo diode.

11. The apparatus as recited in claim 7 wherein the transmitting means includes a laser tunable having an output tunable to many wavelengths.

12. The apparatus as recited in claim 7 wherein the indicating means includes a memory containing a table with having values indicating fiber type as a function of pulse width and fiber length.

13. An apparatus for distinguishing between fiber types having different dispersion characteristics comprising:

means for transmitting through a test fiber an optical pulse at a plurality of predetermined wavelengths and having pulse width;

means for filtering at the plurality of predetermined wavelengths the optical pulse propagating through the test fiber;

means for detecting the pulse width of the filtered optical pulse at each of the plurality of predetermined wavelengths;

means for determining the filtered optical pulse having the smallest pulse width; and means for indicating that the test fiber has a first dispersion characteristic by correlating the filtered optical pulse having the smallest pulse width to its respective filter's predetermined wavelength.

14. The apparatus as recited in claim 13 wherein the means for transmitting includes an optical source having a broad spectrum output coupled to a filter bank.

15. The apparatus as recited in claim 13 wherein the means for transmitting the optical pulse includes a tunable laser.

* * * * *